United States Patent
Siffert (12)

(10) Patent No.: US 6,251,853 B1
(45) Date of Patent: Jun. 26, 2001

(54) PTX SENSITIVE G PROTEINS, THE PRODUCTION AND USE THEREOF

(76) Inventor: Winfried Siffert, Schönleinstr. 49, 45147 Essen (DE)

( * ) Notice: Subject to any disclaimer, the term of this patent is extended or adjusted under 35 U.S.C. 154(b) by 0 days.

(21) Appl. No.: 09/147,826

(22) PCT Filed: Aug. 29, 1997

(86) PCT No.: PCT/EP97/04709

§ 371 Date: Mar. 15, 1999

§ 102(e) Date: Mar. 15, 1999

(87) PCT Pub. No.: WO98/11212

PCT Pub. Date: Mar. 19, 1998

(30) Foreign Application Priority Data

Sep. 13, 1996 (DE) ............................................. 196 37 518

(51) Int. Cl.⁷ .................................................. C02K 14/00
(52) U.S. Cl. ................................ 514/2; 514/12; 530/350
(58) Field of Search ................................ 530/350; 514/12, 514/2

(56) References Cited

FOREIGN PATENT DOCUMENTS 9704709    8/1997    (WO) .

OTHER PUBLICATIONS

Lee, et al., "A Third Form of the G Protein β Subunit," *The Journal of Biological Chemistry*, Jun. 22, 1992, pp. 24776–24781.

Levine, et al., "Molecular cloning of β3 subunit, a third form of the G protein β–subunit polypeptide," *Proc. Natl. Acad. Sci.*, Mar. 19910, pp. 2329–2333.

Kleuss, et al., "Different β–subunits determine G–protein interaction with transmembrane receptors," *Letters to Nature*, Jul. 30, 1992, vol. 358, pp. 424–426.

Siffert, et al., "Enhanced G Protein Activation in Immortalized Lymphoblasts from Patients with Essential Hypertension," *J. Clin. Invest*, Aug. 1995, vol. 96, pp. 759–766.

Roche, e tal., "abolition of G protein inhibition of $\alpha_{1A}$ and $\alpha_{1B}$ calcium channels by co–expression of the $\beta_3$ subunit," *FEBS Letters*, 1995, pp. 43–46.

*Primary Examiner*—Karen Cochrane Carlson
(74) *Attorney, Agent, or Firm*—Nixon Peabody LLP; David S. Safran

(57) ABSTRACT

The beta-3 subunit of a human G protein which consists of not more than six WD repeat motifs is described.

3 Claims, 5 Drawing Sheets

PTX SENSITIVE G PROTEINS, THE PRODUCTION AND USE THEREOF

SUMMARY AND OBJECTS OF THE INVENTION (i) Field of the Invention

The present invention relates to novel human G proteins, in particular β3 subunits of G proteins, a process for their preparation and their use in diagnosis and therapy.

(ii) Description of Related Art

Heterotrimeric guanine nucleotide-binding proteins (G proteins) have an outstanding importance in intracellular signal transduction. They mediate the relaying of extracellular signals after stimulation of hormone receptors and other receptors which undergo a conformational change after receptor activation. This leads to activation of G proteins which may subsequently activate or inhibit intracellular effectors (eg. ion channels, enzymes). Heterotrimeric G proteins consist of three subunits, the α, β and γ subunits. To date, several different α subunits, 5 β subunits and about 12 γ subunits have been detected by biochemical and molecular biological methods (Birnbaumer, L. and Birnbaumer, M. Signaltransduction by G proteins: 1994 edition. J.Recept.Res. 15:213–252, 1995; Offermanns, S. and Schultz, G. Complex information processing by the transmembrane signaling system involving G proteins. Naunyn Schmiedebergs Arch.Pharmacol. 350:329–338, 1994; Nürnberg, B., Gudermann, T., and Schultz, G. Receptors and G proteins as primary components of transmembrane signal transduction. Part 2. G proteins: structure and function. J.Mol.Med. 3:123–132, 1995; Neer, E. J. Heterotrimeric G proteins: Organizers of Transmembrane Signals. Cell 80:249–257, 1995; Rens-Domiano, S. and Hamm, H. E. Structural and functional relationships of heterotrimeric G-proteins. FASEB J. 9:1059–1066, 1995).

Receptor-mediated activation of certain α subunits can be inhibited by pretreatment with pertussis toxin (PTX). These include, in particular, the α isoforms αi1, αi2 and αi3, and various αo subunits. G Proteins of these types are also referred to as PTX-sensitive G proteins.

βγ Subunits carry out essential functions in G protein activation and in the modulation of intracellular reactions. All G protein β subunits disclosed to date have high degrees of homology at the level of the nucleotide sequence and at the level of the amino-acid sequence. Moreover these similarities are found not only within the human β subunits (β1, β2, β3) but also in comparison with β subunits of other species, for example fruit fly or yeast. X-Ray structural analyses have been able to determine those amino acids in α, β and γ subunits which are in contact with one another and are necessary for ordered formation of the heterotrimer.

All G protein β subunits disclosed to date belong to the WD repeat proteins. The N terminus of the β subunit interacts predominantly with γ subunits, and the C terminus is involved in the interaction with receptors.

β Subunits form what are called propeller structures. The β propellers of the Gβ subunits consist of 7 β propeller blades, each propeller blade consisting of 4 amino-acid regions in antiparallel arrangement. The seven-fold symmetry of the β propeller can be detected at the level of the amino-acid sequence, which comprises 7 WD repeats. A WD repeat motif comprises about 40 amino acids and has a number of conserved amino acids, including Trp-Asp dipeptide sequences This WD motif frequently terminates the WD repeat (FIG. 1).

SUMMARY AND OBJECTS OF THE INVENTION

It has now been found, surprisingly, that G protein β3 subunits which consist only of 6 instead of the 7 WD repeat motifs otherwise described occur, for example, in hypertensives. The cellular activatability of PTX-sensitive G proteins is increased in these hypertensives compared with normotensives.

Molecular analysis revealed a novel amino-acid sequence for the β3 subunit in these hypertensives, being shorter by 41 amino acids than the known sequence. The sequence is depicted in SEQ ID NO:2. Formally, it is derived from the known human β3 subunit by deletion of amino acids 167–207.

The corresponding DNA sequence coding therefor is described in SEQ ID NO:1.

The reason for the occurrence of the shortened Gβ3 subunit in hypertensives is presumably an alternative splicing of the relevant gene. At the DNA level, there is an intron exactly in front of the putative splicing site. The intron starts behind nucleotide 497 in the open reading site (numbering as in SEQ ID NO;1).

It was also possible by PCR on genomic DNA to detect an intron starting at about nucleotide 620. The shortened form apparently comes about through deletion of a complete exon. The invention furthermore relates to a process for preparing shortened forms of human Gβ3 subunits as mentioned above by expression of a nucleic acid sequence coding therefor in a host organism.

The recombinant expression preferably takes place by preparing a gene construct which, besides the coding nucleic acid sequence, also comprises other signal and regulatory sequences such as promoters, terminators, ribosome binding sites, polyadenylation sites and the like. The general procedure for recombinant expression of a gene is familiar to the skilled worker.

The invention furthermore relates to the use of the nucleic acid sequences according to the invention for producing drugs for gene therapy. Introduction of these nucleic acid sequences in direct form or after preparation of an appropriate gene vector into patients' cells is able to achieve an increased activatability of G proteins therein.

This is desirable in a number of disorders in which there is dysregulation associated with G protein.

Diseases associated with G protein dysregulation mean those disorders in which G protein is involved in signal transduction and does not perform its function in a physiological manner.

These disorders include cardiovascular disorders, metabolic disturbances and immunoloigcal disorders.

Cardiovascular disorders which should be mentioned are: hypertension, pregnancy hypertension (gestosis, hypertension in pregnancy), coronary heart disease, localized and/or generalized atherosclerosis, stenoses of blood vessels, restenosis after revascularizing interventions on vessels (eg. PTCA with and without stent implantation), proneness to stroke, thrombophilia and increased platelet aggregation.

Metabolic disturbances which should be mentioned are: metabolic syndrome, insulin resistance and hyperinsulinemia, type II diabetes mellitus, diabetic complications (eg. nephropathy, neuropathy, retinopathy, etc.), lipid metabolism disturbances, disturbances of central chemoreception ($CO_2$ tolerance, acidosis tolerance, sudden infant death (SIDS)).

Immunologial disorders which should be mentioned are; impaired strength of the body's immune response (formation of immunoglobulins, aggressiveness of T cells and NK cells), impaired general tendency to proliferation, including wound-healing capacity, tendency to tumor development and proliferation including metastatic potential of malignantly transformed cells, duration of the latency period after HIV infection until the disorder becomes clinically apparent, Kaposi sarcoma, tendency to cirrhosis of the liver, transplant tolerance and transplant rejection.

The invention furthermore relates to the use of the nucleic acid sequences according to the invention for the diagnosis of disorders, in particular including determination of the risk of suffering from a disease associated with G protein dysregulation.

Besides determining the risk of certain disorders, it is also possible to make general physiological data and statements through the use according to the invention, for example on central chemoreception, $CO_2$ tolerance, acidosis tolerance, risk of sudden infant death (SIDS), fitness for certain types of sport.

The invention furthermore relates to the use of nucleic acid sequences which are complementary to the nucleic acid sequences coding for the shortened form of the Gβ3 subunit. Sequences of this type can be used as antisense constructs for the treatment or prevention of disorders associated with G protein dysregulation.

The invention furthermore relates to a method for determining a relative risk of suffering from diseases associated with G protein dysregulation for a subject by comparing the gene sequence for human G protein β3 subunit of the subject with the gene sequence SEQ ID NO: 1 and, in the event that it coincides with SEQ ID NO: 1, assigning an increased risk to the subject.

In the method according to the invention for determining the relative risk, body material containing the subject's genetic information is taken from the subject. This is achieved, as a rule, by isolating the nucleic acid from a blood sample.

The structure of the gene for the G protein β3 subunit is determined from the subject's isolated nucleic acid and compared with the sequence indicated in SEQ ID NO:1.

The structure of the gene can be determined by sequencing the nucleic acid. This can take place either directly from the genomic DNA or after amplification of the nucleic acid, for example by the PCR technique.

The structure of the gene can take place at the mRNA or cDNA level.

Determination is preferably by sequencing after PCR amplification of the cDNA. The primers suitable for the PCR reaction [sic] can easily be deduced by the skilled worker from the sequences depicted in SEQ ID NO:1. The procedure for this is advantageously such that in each case a primer binding strand and complementary strand in front of and behind the deletion site is chosen.

However, the comparison of genes can also be carried out by other methods, for example by selective hybridization or by appropriate mapping using restriction enzymes.

The diagnostic methods described above can also be carried out at the protein level. For example, the proteins according to the invention can be used to produce specific antibodies to recognize the shortened form of the Gβ3 subunit. Antibodies of this type can then be used to carry out, where appropriate, by conventional ELISA methods, protein chemical investigations in addition or alternatively to the genetic investigations.

The invention furthermore relates to the production of transgenic animals which harbor the genetic modification described above (shortening of the Gβ3 subunit). Transgenic animals of this type are of great importance in particular as animal models for investigating and treating the diseases described above. Processes for producing transgenic animals are generally known to the skilled worker.

DETAILED DESCRIPTION OF PREFERRED EMBODIMENTS

Figure 2:
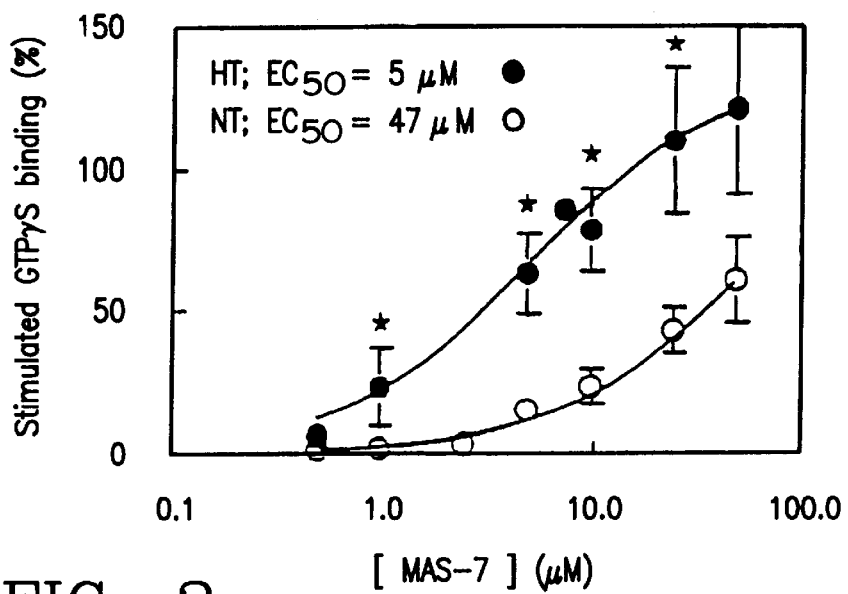
FIG. 2 is a graph depicting the concentration dependence of the G protein activation induced by mastiparan 7 in the normotensive and hypertensive state.

The following Examples serve to illustrate the invention further. Experimental part 1. Functional Results on G Protein Activation in Essential Hypertension A detailed characterization was carried out of the activation of G proteins from cells of normotensive subjects and hypertensive patients. For this purpose, the stimulated incorporation of radiolabeled [$^{35}$S] GTPγS was quantified by the method described by Wieland et al. (Wieland, T., Liedel, K., Xaldenberg-Stasch, S., Meyer zu Heringdorf, D., Schmidt, M., and Jakobs, K. E. Analysis of receptor-G protein interactions in permeabilized cells. Naunyn-Schmiedeberg's Arch.Pharmacol. 351:329–336, 1995). G Proteins were activated initially by stimulating cells which had been permeabilized with digitonin using the peptide mastoparan 7. This peptide simulates the configuration of an activated G protein-coupled receptor so that it can be used to induce direct G protein activation independent of receptors (Ross, E. M. and Higashijima, T. Regulation of G protein activation by mastoparan and other cationic peptides. Methods Enzymol. 237:27–38, 1994). The binding of GTPγS induced by MAS-7 is completely PTX-sensitive so that it can be used to quantify the activation of heterotrimeric G proteins of the Gi type. FIG. 2 shows the concentration-dependence of the G protein activation induced by mastiparan 7 (MAS-7) in the normotensive (NT) and hypertensive (HT) state. MAS-7 induces strong [$^{35}$S] GTPγS binding on HT cells with an EC50 of about 5 μm (FIG. 2). Maximum binding is reached at about 25 to 50 μm MAS-7. In contrast to this, the concentration required for the same [$^{35}$S] GTPγS binding to NT cells are [sic] 10 times higher (FIG. 2). These data demonstrate that activation of PTX-sensitive G proteins in HT cells requires distinctly less activated receptor than that in NT cells.

Figure 3:
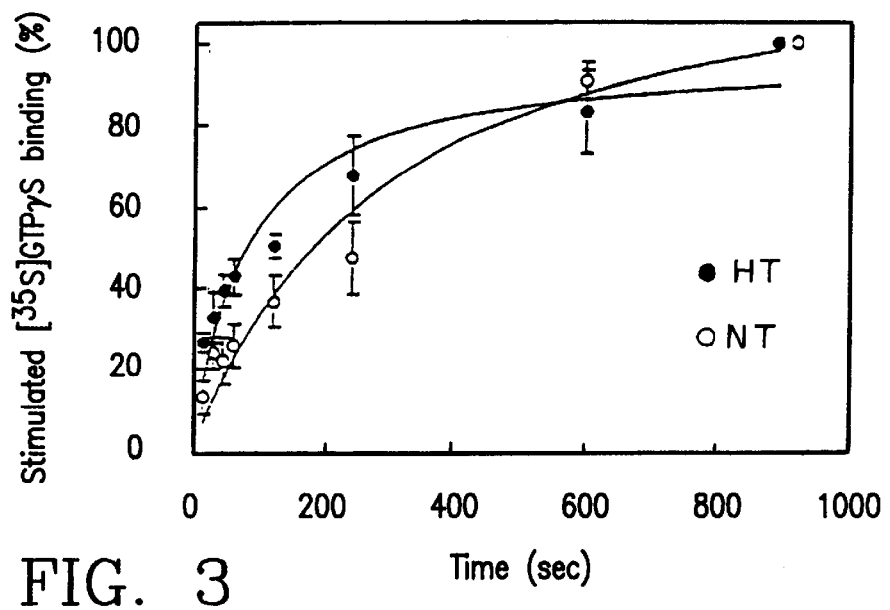
FIG. 3 is a graph depicting the time course of binding, stimulated by mastoparan 7 of [$^{35}$S] GTPαS to cell lines from normotensives and hypertensives.

FIG. 3 shows the time course of the binding, stimulated by mastoparan 7, of [$^{35}$S] GTPγS to cell lines from normotensives (NT) and hypertensives (HT).

The binding of [$^{35}$S] GTPγS to hypertensive cells is distinctly speeded up (rate constants 0.005 s$^{-1}$ in the normotensive versus 0.01 s$^{-1}$ in the hypertensive state).

Figure 4:
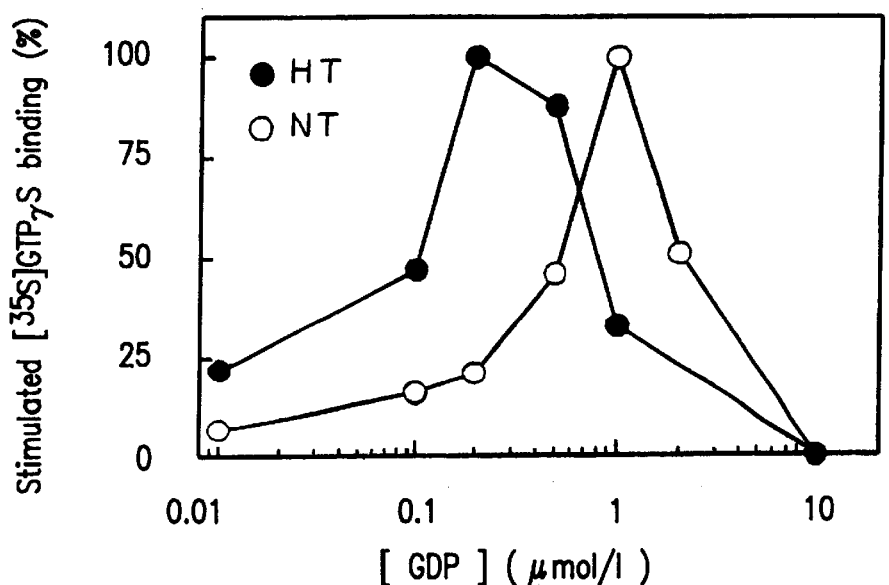
FIG. 4 is a graph depicting the GDP dependence of binding, stimulated by mastoparan 7, of [$^{35}$S] GTPαS to isolated cell membranes from normotensives and hypertensives.

FIG. 4 shows the GDP-dependence of binding, stimulated by mastoparan 7, of [$^{35}$S] GTPγS to isolated cell membranes from normotensives and hypertensives. It is evident that the maximum stimulated binding of [$^{35}$S] GTPγS to membranes from hypertensives occurs at lower concentrations of GDP (about 0.2 μmol/l), where a concentration of 1 μmol/l GDP is required for the same effect in normotensives.

Figure 5:
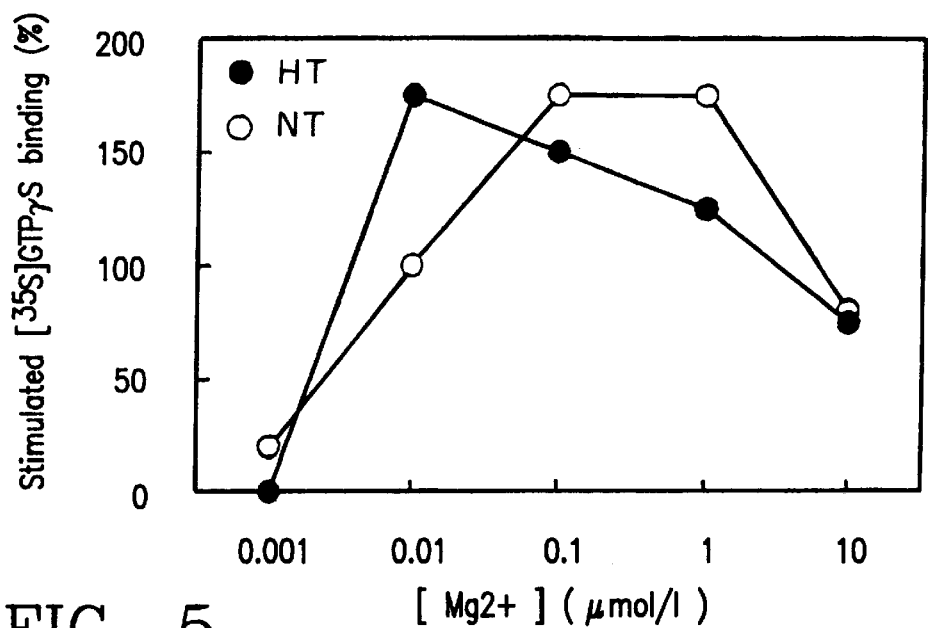
FIG. 5 is a graph depicting $Mg^{27}$ dependence of the binding, stimulated by Mastoparan 7, of [$^{35}$S] GTPαS to membranes from cells from normotensives and hypertensives.

In a similar way, the maximum binding, stimulated by mastoparan 7, of [$^{35}$S] GTPγS to membrane preparations from hypertensive cells a low concentration of free Mg$^{2+}$ (about 0.01 mmol/l), while a free Mg$^{2+}$ concentration of 0.1 mmol/l is necessary for the same maximum binding of [$^{35}$S] GTPγS to membranes from normotensive cells (FIG. 5).

Experiments were subsequently carried out on the reconstitution of the increased activatability of G proteins from hypertensive cells. For this purpose, the photoreceptor rhodopsin, and the G protein α subunit transducin (αt) from the bovine eye were purified (Phillips, W. J., Wong, S. C., and Cerione, R. A.

Rhodopsin/transducin interactions. II. Influence of the transducin-βγ subunit complex on the coupling of the transducin-a subunit to rhodopsin. J.Biol.Chem. 267:17040–17046, 2992). In addition, G proteins were extracted from membranes from normotensive and hypertensive cells by addition of cholate (Mitchell, J., Northup, J. K., and Schimmer, B. P. Defective guanyl nucleotidebinding protein βγ subunits in a forskolin-resistant mutant of the Y1 adrenocortical cell line. Proc.Natl.Acad.Sci.U.S.A. 89(19): 8933–9937, 1992). The specific binding, induced by rhodopsin (=receptor), of [$^{35}$S] GTPγS to α-transducin (αt) was measured, and the effect of cholate extracts from membranes of normotensive and hypertensive cells on this binding was investigated. The protein concentration in the cholate extracts was identical in all the experiments.

Figure 6:
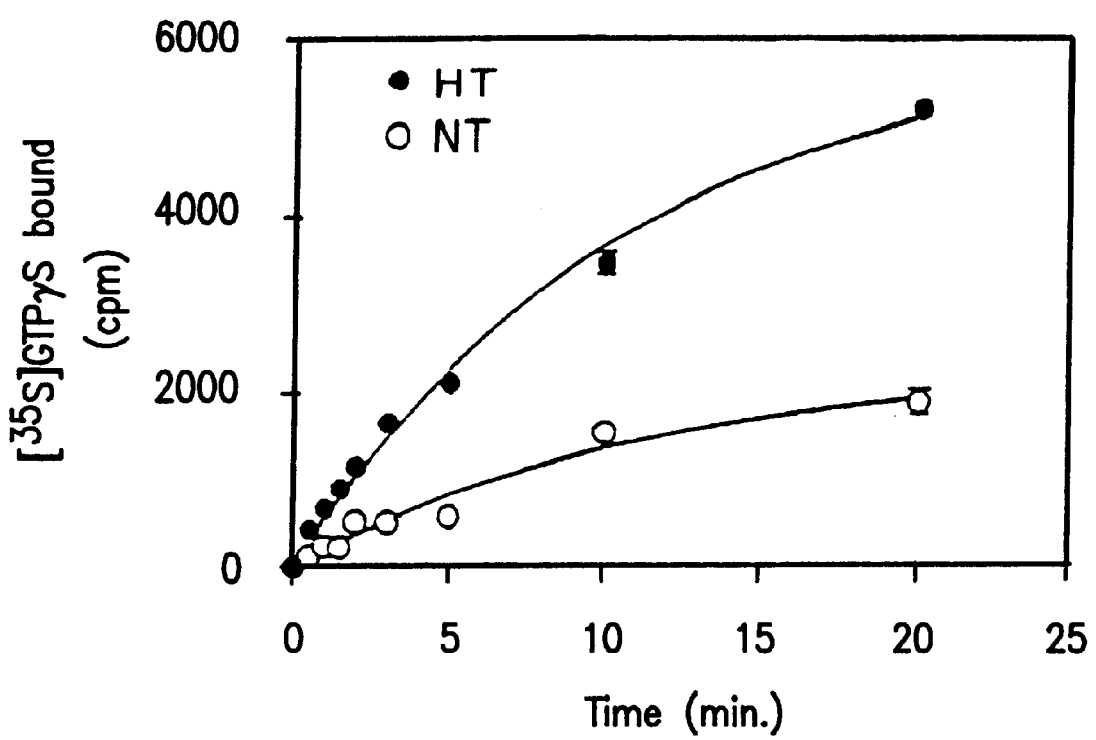
FIG. 6 is a graph depicting the effect of cholate extracts from normotensive and hypertensive cells on the binding, stimulated by rhodospin, of [$^{35}$S] GTPαS, to αt.

FIG. 6 shows the effect of cholate extracts from normotensive and hypertensive cells on the binding, stimulated by rhodopsin, of [$^{35}$S] GTPγS, to αt.

It is clear in this case that cholate extracts from hypertensive cells promote the rhodopsin-catalyzed binding of [$^{35}$S] GTPγS to αt distinctly more than on mediation by cholate extracts from normotensives.

The experiments which are shown permit the following conclusions to be drawn:

There is increased activatability of G proteins in hypertensive cells. This is more efficient by comparison with G protein activation in normotensive cells in that hypertensive cells require distinctly less activated receptor and, in addition, the kinetics of G protein activation are distinctly speeded up (FIGS. 2 and 3).

Moreover, maximum G protein activation requires distinctly lower concentrations of free GDP and free Mg$^{2+}$ in the case of hypertensive cells than in normotensive cells. This leads to the conclusion that the protein interactions of α, β and γ subunits take place distinctly more efficiently in hypertensive cells than in normotensive cells (FIGS. 4 and 5).

The rhodopsin-catalyzed binding of [$^{35}$S] GTPγS to αt is enhanced distinctly more by cholate extracts from hypertensive cells than by cholate extracts from normotensive cells. This proves that the enhanced G protein activation in the case of hypertensive cells can be reconstituted in an in vitro system (FIG. 6). Moreover, it is possible unambiguously to conclude from these findings that the underlying alteration in hypertensive cells is to be found in the βγ subunits of heterotrimeric G proteins. In said reconstitution system there is no activation of the α subunits still present in the cholate extracts in the presence of αt. Moreover, the added photoreceptor rhodopsin specifically activates only the added αt but not the a subunits remaining endogenously in cholate extracts.

Figure 1:
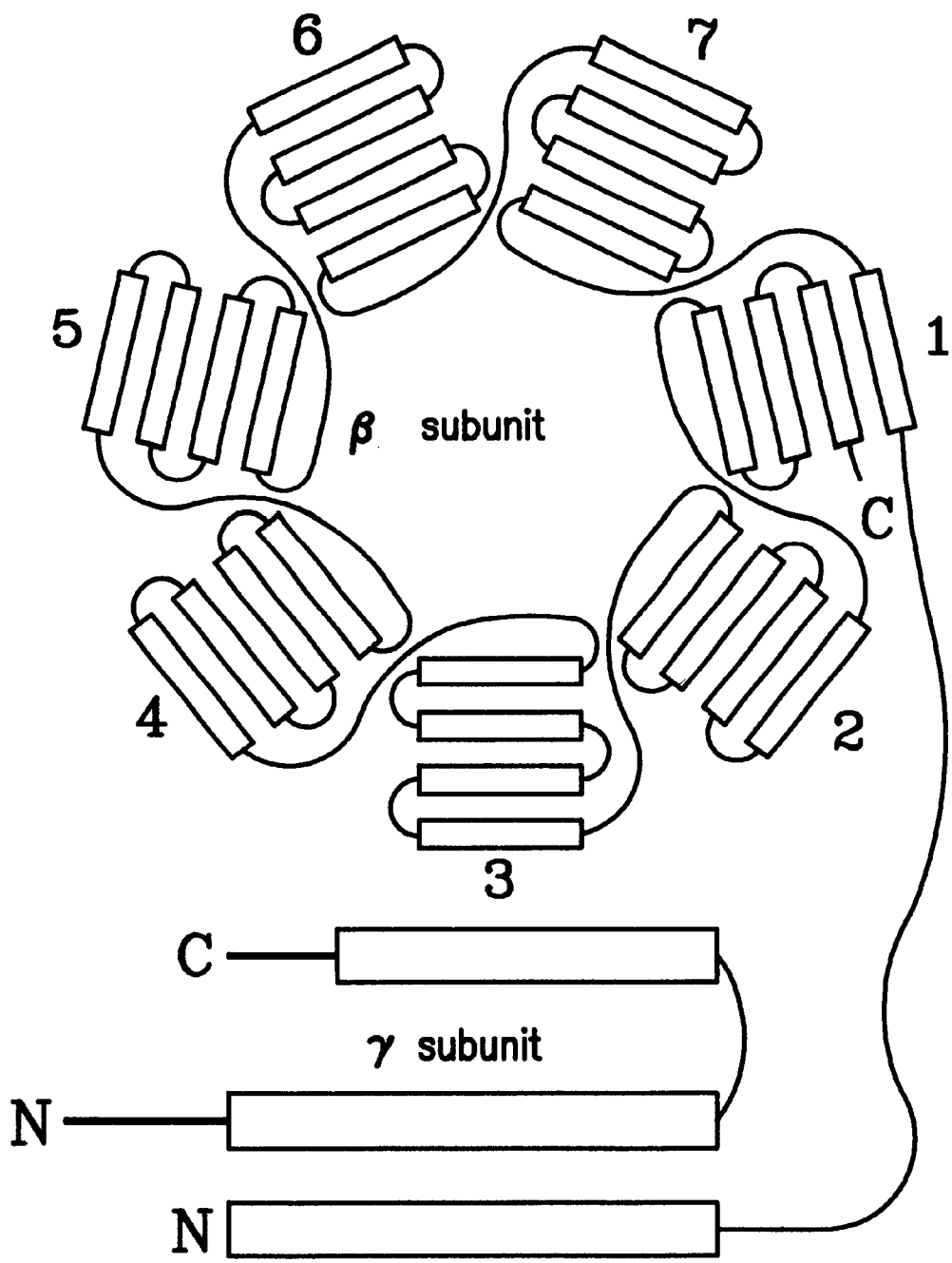
FIG. 1 depicts the structure of G protein β subunits and interaction with α subunits.
Figure 7:
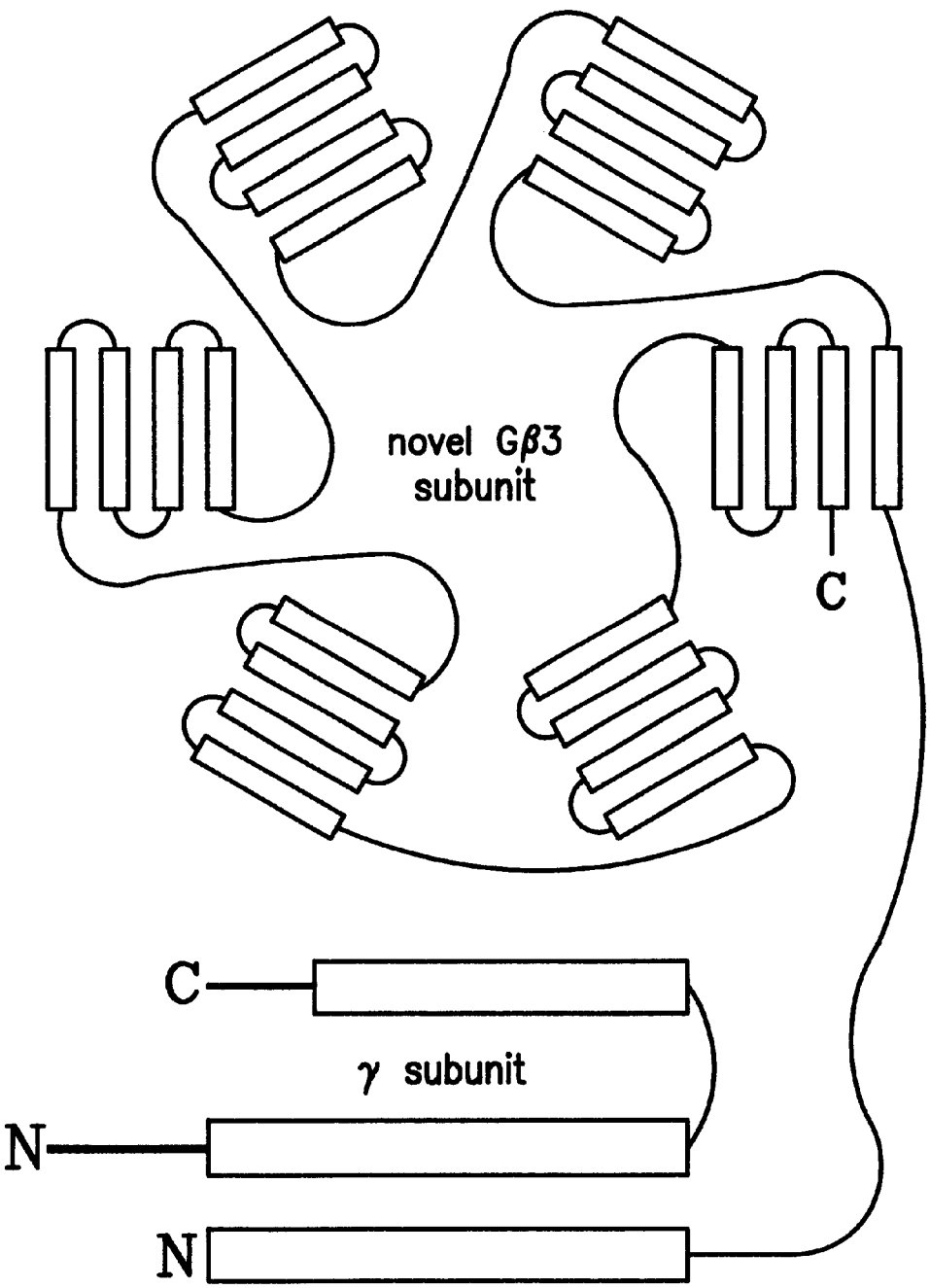
FIG. 7 depicts the structure of the novel variant of human GB3 protein.

The novel protein consists of 299 amino acids. Compared with the human Gβ3 subunit previously described there is a deletion in the region of the 4th WD repeat. However, because of the regularity of the sequence of certain amino acids, it can be predicted that the novel, short Gβ3 protein will likewise form a proper propeller structure, but this new propeller would now consist of 6 propeller blades (FIG. 7), no longer of seven (FIG. 1).

Since both the N terminus and the C terminus of the novel, short Gβ3 subunits are unchanged from the previously known Gβ3 subunit, it is possible to predict unimpaired interaction with α and γ subunits of heterotrimeric G proteins and with coupling receptors. It is evident, in connection with the functional results described above, that the novel, short Gβ3 subunit functionally mediates the increased activation of heterotrimeric G proteins observed in hypertensives.

The reason for the occurrence of the shortened Gβ3 subunits in hypertensives is assumed to be an alternative splicing of the gene coding for human Gβ3. In fact at the DNA level there is an intron exactly in front of the putative splicing site.

The intron starts behind base 497 in the open reading frame when the A of the ATG start codon is defined as +1.

The intron limits and the branch site are shown in italics and underlined.

GGA CAC CAC GTG *gtgaggctgaacattgctggtgctggggcttgggagtgggcccgg* cctttc *tctaac*agtctccctccattttggcag TGC CTT GTG GGA Since an intron can also be detected starting at about base 620 in the open reading frame by PCR on genomic DNA, the shortened form of human Gβ3 described herein is evidently the result of an alternative splicing of the original Gβ3, resulting in deletion of a complete exon.

What is claimed is:

1. Beta-3 subunit of a human G protein comprising not more than six WD repeat motifs.

2. A protein as claimed in claim 1, comprising the amino-acid sequence depicted in SEQ ID NO: 2.

3. A vector comprising the nucleic acid sequence of claim 2 operably linked to a regulatory signal permitting expression in a host.

* * * * *

SEQUENCE LISTING

<160> NUMBER OF SEQ ID NOS: 2

<210> SEQ ID NO: 1
<211> LENGTH: 1394
<212> TYPE: DNA
<213> ORGANISM: Homo sapiens
<220> FEATURE:
<221> NAME/KEY: CDS
<222> LOCATION: (1)..(897)

-continued

```
<400> SEQUENCE: 1 atg ggg gag atg gag caa ctg cgt cag gaa gcg gag cag ctc aag aag        48
Met Gly Glu Met Glu Gln Leu Arg Gln Glu Ala Glu Gln Leu Lys Lys
1               5                   10                  15 cag att gca gat gcc agg aaa gcc tgt gct gac gtt act ctg gca gag        96
Gln Ile Ala Asp Ala Arg Lys Ala Cys Ala Asp Val Thr Leu Ala Glu
            20                  25                  30 ctg gtg tct ggc cta gag gtg gtg gga cga gtc cag atg cgg acg cgg       144
Leu Val Ser Gly Leu Glu Val Val Gly Arg Val Gln Met Arg Thr Arg
        35                  40                  45 cgg acg tta agg gga cac ctg gcc aag att tac gcc atg cac tgg gcc       192
Arg Thr Leu Arg Gly His Leu Ala Lys Ile Tyr Ala Met His Trp Ala
    50                  55                  60 act gat tct aag ctg ctg gta agt gcc tcg caa gat ggg aag ctg atc       240
Thr Asp Ser Lys Leu Leu Val Ser Ala Ser Gln Asp Gly Lys Leu Ile
65                  70                  75                  80 gtg tgg gac agc tac acc acc aac aag gtg cac gcc atc cca ctg cgc       288
Val Trp Asp Ser Tyr Thr Thr Asn Lys Val His Ala Ile Pro Leu Arg
                85                  90                  95 tcc tcc tgg gtc atg acc tgt gcc tat gcc cca tca ggg aac ttt gtg       336
Ser Ser Trp Val Met Thr Cys Ala Tyr Ala Pro Ser Gly Asn Phe Val
            100                 105                 110 gca tgt ggg ggg ctg gac aac atg tgt tcc atc tac aac ctc aaa tcc       384
Ala Cys Gly Gly Leu Asp Asn Met Cys Ser Ile Tyr Asn Leu Lys Ser
        115                 120                 125 cgt gag ggc aat gtc aag gtc agc cgg gag ctt tct gct cac aca ggt       432
Arg Glu Gly Asn Val Lys Val Ser Arg Glu Leu Ser Ala His Thr Gly
    130                 135                 140 tat ctc tcc tgc tgc cgc ttc ctg gat gac aac aat att gtg acc agc       480
Tyr Leu Ser Cys Cys Arg Phe Leu Asp Asp Asn Asn Ile Val Thr Ser
145                 150                 155                 160 tcg ggg gac acc acg tgt gcc aag ctc tgg gat gtg cga gag ggg acc       528
Ser Gly Asp Thr Thr Cys Ala Lys Leu Trp Asp Val Arg Glu Gly Thr
                165                 170                 175 tgc cgt cag act ttc act ggc cac gag tcg gac atc aac gcc atc tgt       576
Cys Arg Gln Thr Phe Thr Gly His Glu Ser Asp Ile Asn Ala Ile Cys
            180                 185                 190 ttc ttc ccc aat gga gag gcc atc tgc acg ggc tcg gat gac gct tcc       624
Phe Phe Pro Asn Gly Glu Ala Ile Cys Thr Gly Ser Asp Asp Ala Ser
        195                 200                 205 tgc cgc ttg ttt gac ctg cgg gca gac cag gag ctg atc tgc ttc tcc       672
Cys Arg Leu Phe Asp Leu Arg Ala Asp Gln Glu Leu Ile Cys Phe Ser
    210                 215                 220 cac gag agc atc atc tgc ggc atc acg tct gtg gcc ttc tcc ctc agt       720
His Glu Ser Ile Ile Cys Gly Ile Thr Ser Val Ala Phe Ser Leu Ser
225                 230                 235                 240 ggc cgc cta cta ttc gct ggc tac gac gac ttc aac tgc aat gtc tgg       768
Gly Arg Leu Leu Phe Ala Gly Tyr Asp Asp Phe Asn Cys Asn Val Trp
                245                 250                 255 gac tcc atg aag tct gag cgt gtg ggc atc ctc tct ggc cac gat aac       816
Asp Ser Met Lys Ser Glu Arg Val Gly Ile Leu Ser Gly His Asp Asn
            260                 265                 270 agg gtg agc tgc ctg gga gtc aca gct gac ggg atg gct gtg gcc aca       864
Arg Val Ser Cys Leu Gly Val Thr Ala Asp Gly Met Ala Val Ala Thr
        275                 280                 285 ggt tcc tgg gac agc ttc ctc aaa atc tgg aac tgaggaggct ggagaaaggg    917
Gly Ser Trp Asp Ser Phe Leu Lys Ile Trp Asn
    290                 295 aagtggaagg cagtgaacac actcagcagc cccctgcccg accccatctc attcaggtgt    977
```

-continued

```
tctcttctat attccgggtg ccattcccac taagctttct cctttgaggg cagtggggag   1037
catgggactg tgcctttggg aggcagcatc agggacacag gggcaaagaa ctgccccatc   1097
tcctcccatg gccttccctc cccacagtcc tcacagcctc tcccttaatg agcaaggaca   1157
acctgcccct ccccagccct ttgcaggccc agcagacttg agtctgaggc cccaggccct   1217
aggattcctc cccagagcc actacctttg tccaggcctg ggtggtatag ggcgtttggc   1277
cctgtgacta tggctctggc accactaggg tcctggccct cttcttattc atgctttctc   1337 cttttctac cttttttct ctcctaagac acctgcaata aagtgtagca ccctggt        1394
```

<210> SEQ ID NO: 2
<211> LENGTH: 299
<212> TYPE: PRT
<213> ORGANISM: Homo sapiens

<400> SEQUENCE: 2

```
Met Gly Glu Met Glu Gln Leu Arg Gln Glu Ala Glu Gln Leu Lys Lys
1               5                   10                  15

Gln Ile Ala Asp Ala Arg Lys Ala Cys Ala Asp Val Thr Leu Ala Glu
            20                  25                  30

Leu Val Ser Gly Leu Glu Val Val Gly Arg Val Gln Met Arg Thr Arg
        35                  40                  45

Arg Thr Leu Arg Gly His Leu Ala Lys Ile Tyr Ala Met His Trp Ala
    50                  55                  60

Thr Asp Ser Lys Leu Leu Val Ser Ala Ser Gln Asp Gly Lys Leu Ile
65                  70                  75                  80

Val Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
            100                 105                 110

Ala Cys Gly Gly Leu Asp Asn Met Cys Ser Ile Tyr Asn Leu Lys Ser
        115                 120                 125

Arg Glu Gly Asn Val Lys Val Ser Arg Glu Leu Ser Ala His Thr Gly
    130                 135                 140

Tyr Leu Ser Cys Cys Arg Phe Leu Asp Asp Asn Asn Ile Val Thr Ser
145                 150                 155                 160

Ser Gly Asp Thr Thr Cys Ala Lys Leu Trp Asp Val Arg Glu Gly Thr
                165                 170                 175

Cys Arg Gln Thr Phe Thr Gly His Glu Ser Asp Ile Asn Ala Ile Cys
            180                 185                 190

Phe Phe Pro Asn Gly Glu Ala Ile Cys Thr Gly Ser Asp Asp Ala Ser
        195                 200                 205

Cys Arg Leu Phe Asp Leu Arg Ala Asp Gln Glu Leu Ile Cys Phe Ser
    210                 215                 220

His Glu Ser Ile Ile Cys Gly Ile Thr Ser Val Ala Phe Ser Leu Ser
225                 230                 235                 240

Gly Arg Leu Leu Phe Ala Gly Tyr Asp Asp Phe Asn Cys Asn Val Trp
                245                 250                 255

Asp Ser Met Lys Ser Glu Arg Val Gly Ile Leu Ser Gly His Asp Asn
            260                 265                 270

Arg Val Ser Cys Leu Gly Val Thr Ala Asp Gly Met Ala Val Ala Thr
        275                 280                 285

Gly Ser Trp Asp Ser Phe Leu Lys Ile Trp Asn
    290                 295
```